United States Patent
Hirano et al.

(10) Patent No.: US 7,485,369 B2
(45) Date of Patent: Feb. 3, 2009

(54) SODIUM HYDROGENCARBONATE CRYSTAL PARTICLES HAVING LOW CAKING PROPERTY AND PROCESS FOR PRODUCING THEM

(75) Inventors: Hachirou Hirano, Ichihara (JP); Takako Hirano, legal representative, Chiba (JP); Shintaro Kikuchi, Kashima-gun (JP); Fumiaki Nakashima, Kashima-gun (JP); Hisakazu Arima, Kashima-gun (JP); Shigeru Sakurai, Chiyoda-ku (JP)

(73) Assignee: Asahi Glass Company, Limited, Tokyo (JP)

( * ) Notice: Subject to any disclaimer, the term of this patent is extended or adjusted under 35 U.S.C. 154(b) by 105 days.

(21) Appl. No.: 11/619,411

(22) Filed: Jan. 3, 2007

(65) Prior Publication Data

US 2007/0104635 A1    May 10, 2007

Related U.S. Application Data

(63) Continuation of application No. PCT/JP2005/012107, filed on Jun. 30, 2005.

(30) Foreign Application Priority Data

Jul. 1, 2004    (JP) .............................. 2004-195996

(51) Int. Cl.
*B32B 5/16* (2006.01)
*C01D 1/22* (2006.01)
*C01D 7/12* (2006.01)

(52) U.S. Cl. .................. 428/403; 423/186; 423/307; 423/641

(58) Field of Classification Search ................ 428/402, 428/403; 423/186, 307, 641
See application file for complete search history.

(56) References Cited

U.S. PATENT DOCUMENTS

| | | | | |
|---|---|---|---|---|
| 3,647,365 A | * | 3/1972 | Saeman | 423/209 |
| 4,151,266 A | * | 4/1979 | Robey et al. | 423/425 |
| 6,833,346 B1 | * | 12/2004 | Morrison et al. | 510/444 |
| 7,361,318 B2 | * | 4/2008 | Yokoyama et al. | 423/184 |
| 2003/0211027 A1 | | 11/2003 | Yokohama et al. | |
| 2006/0193765 A1 | | 8/2006 | Nakashima et al. | |
| 2007/0104635 A1 | * | 5/2007 | Hirano et al. | 423/422 |
| 2007/0178037 A1 | * | 8/2007 | Hirano et al. | 423/422 |

FOREIGN PATENT DOCUMENTS

| | | |
|---|---|---|
| JP | 2-275714 | 11/1990 |
| JP | 4-270113 | 9/1992 |
| JP | 5-58622 | 3/1993 |
| JP | 2001-171045 | 6/2001 |
| JP | 3306873 | 5/2002 |
| JP | 2003-104722 | 4/2003 |

OTHER PUBLICATIONS

U.S. Appl. No. 11/616,296, filed Dec. 27, 2006, Hirano et al.
U.S. Appl. No. 11/619,411, filed Jan. 3, 2007, Hirano et al.

* cited by examiner

*Primary Examiner*—H. T Le
(74) *Attorney, Agent, or Firm*—Oblon, Spivak, McClelland, Maier & Neustadt, P.C.

(57) ABSTRACT

Sodium hydrogencarbonate crystal particles, which comprise sodium hydrogencarbonate crystal particles having an average particle size of from 50 to 500 μm based on the mass, and anhydrous sodium carbonate, and sodium carbonate monohydrate and/or Wegscheider's salt, present on the surface of the sodium hydrogencarbonate crystal particles in such amounts that the total content of anhydrous sodium carbonate, sodium carbonate monohydrate, Wegscheider's salt and sodium sesquicarbonate in the sodium hydrogencarbonate crystal particles is from 0.04 to 1 mass % as calculated as anhydrous sodium carbonate, anhydrous sodium carbonate accounts for at least 40 mass % of the total content, and sodium carbonate monohydrate and/or Wegscheider's salt accounts for from 5 to 60 mass % of the total content. Sodium hydrogencarbonate crystal particles having a low caking property, which are useful in the field of food products, pharmaceuticals, bath additives, etc., which require no necessity to contain an anticaking agent, a process for producing them and a method for packaging them, can be provided.

7 Claims, No Drawings

SODIUM HYDROGENCARBONATE CRYSTAL PARTICLES HAVING LOW CAKING PROPERTY AND PROCESS FOR PRODUCING THEM

TECHNICAL FIELD

The present invention relates to sodium hydrogencarbonate crystal particles having a low caking property which are useful particularly in the field of food products, pharmaceuticals, etc. and which require no necessity to contain an anticaking description agent, a process for producing them and a method for packaging them.

BACKGROUND ART

Sodium hydrogencarbonate ($NaHCO_3$ which is also called baking soda or sodium bicarbonate) is widely used in the field of various food products, as ingredient of baking powder, an additive for soft drinks, etc., in the pharmaceutical industry as a dialysate, an antacid, etc., and further as a fire-extinguishing agent, as a bath additive, as a detergent, as a blasting medium, as an acidic gas neutralizing agent, etc. In most cases, such sodium hydrogencarbonate is produced and packaged, delivered, transported, stored and used in the form of powdery or granular crystal particles.

However, commercial crystal particles of sodium hydrogencarbonate generally show a caking property and has a high caking property resulting from sodium carbonate formed by drying in the production process, especially in an environment at a high temperature with a high humidity. This tendency is remarkable particularly in the rainy season. If caking occurs, the flowability of the particles will be low, and the handling efficiency will deteriorate remarkably in the respective steps from distribution to use, and various troubles are brought about. Thus, the caking is a serious problem which may impair the commercial value of sodium hydrogencarbonate.

Heretofore, in order to prevent the caking of sodium hydrogencarbonate crystal particles, e.g. Patent Document 1 proposes to incorporate various anticaking agents, such as stearates, carbonates, phosphates, silicates, kaolin, talc or silicon dioxide.

However, such a conventional method for incorporating an anticaking agent, not only requires a cost for the anticaking agent or a step of its incorporation, but also requires selection of the type of the anticaking agent depending upon the particular application. Further, for food products, pharmaceuticals, etc., it is impossible to use it, or its amount of use may be limited.

Further, Patent Document 2 discloses a method for producing sodium hydrogencarbonate crystals having a reduced caking property, by drying sodium hydrogencarbonate at from 20 to 60° C. by heated air. However, since the drying temperature is low, the treatment efficiency of a drying apparatus tends to be low, the drying apparatus tends to be large, or the drying time tends to be long.

Further, Patent Document 3 discloses a method for producing sodium hydrogencarbonate crystals having a reduced caking property, which comprises making sodium sesquicarbonate be present on the surface of sodium hydrogencarbonate crystal particles. However, in order to convert sodium hydrogencarbonate to sodium sesquicarbonate, treatment with a high humidity in a long time is required, and accordingly the equipment tends to be large. Further, in the case of treatment at a temperature of at least 30° C. to shorten the treatment time, the temperature and the humidity at the time of conversion into sodium sesquicarbonate greatly vary depending upon the carbon dioxide gas concentration in the atmosphere, and accordingly the carbon dioxide gas concentration, the humidity and the temperature must be controlled with very high accuracy.

Patent Document 1: JP-A-5-58622
Patent Document 2: Japanese Patent No. 3306873
Patent Document 3: JP-A-2003-104722

DISCLOSURE OF THE INVENTION

Under these circumstances, it is an object of the present invention to provide sodium hydrogencarbonate crystal particles having a low caking property, capable of preventing the caking property without use of an anticaking agent which will bring about an increase in cost by its addition and cause various problems along with its use, and capable of reducing the caking property easily and effectively without requiring a long treatment time in their production process, a process for producing them and a method for packaging them.

Further, the present invention provides a packaging method capable of preventing caking of sodium hydrogencarbonate crystal particles having a low caking property thus obtained over a long period of time.

MEANS TO ACCOMPLISH THE OBJECT

The present inventors have conducted extensive studies on prevention of caking of sodium hydrogencarbonate crystal particles and as a result, found that the caking property of sodium hydrogencarbonate crystal particles can be reduced based on the following studies and findings.

Namely, on the surface of sodium hydrogencarbonate crystal particles, depending upon various conditions such as the temperature, the humidity and the carbon dioxide gas concentration, of a gas of an atmosphere in the drying step, or in a case where the crystal particles are discharged from the drying step, with which the particles are to be in contact, a very small amount of sodium hydrogencarbonate is decomposed into anhydrous sodium carbonate ($Na_2CO_3$), and further converted into sodium carbonate monohydrate ($Na_2CO_3.H_2O$) or Wegscheider's salt ($Na_2CO_3.3NaHCO_3$) and then converted into sodium sesquicarbonate ($Na_2CO_3$—$NaHCO_3.2H_2O$). The conversion of anhydrous sodium carbonate into sodium sesquicarbonate via sodium carbonate monohydrate is disclosed in American Chemical Society, monograph series, "MANUFACTURE OF SODA", second edition, Chapter XXIX, Behavior of Soda Ash in Storage, pages 509 to 515 (published by Reinhold Publishing, 1942).

Further, according to the studies by the present inventors, it has been confirmed that caking occurs when, on the surface of sodium hydrogencarbonate crystal particles, anhydrous sodium carbonate is converted into sodium carbonate monohydrate or Wegscheider's salt, or anhydrous sodium carbonate is converted into sodium sesquicarbonate via sodium carbonate monohydrate or Wegscheider's salt. It has been found that relatively weak caking occurs in the former case of conversion of anhydrous sodium carbonate into sodium carbonate monohydrate or Wegscheider's salt, but stronger caking occurs in the latter case of conversion of anhydrous sodium carbonate into the final product sodium sesquicarbonate. This is considered to result from crosslinking of the crystal particles at points where they are in contact, since not only the crystals themselves change but also their volume and mass increase by the above conversion, as shown in the following Table 1. The changes in the volume and the mass of the crystals are more significant when anhydrous sodium carbonate is converted into sodium sesquicarbonate than when anhydrous sodium carbonate is converted into sodium carbonate monohydrate or Wegscheider's salt. This is empirically understood from the fact that the degree of caking is substantially in proportion thereto.

TABLE 1

|  | Anhydrous sodium carbonate | Sodium carbonate monohydrate | Wegscheider's salt | Sodium sesquicarbonate |
|---|---|---|---|---|
| Formula weight | 105.99 | 124.00 | 358.01 | 226.03 |
| Density (g/cm$^3$) | 2.533 | 2.259 | 2.334 | 2.044 |
| Mass (g) per 1 mol of Na | 53.0 | 62.0 | 71.6 | 75.3 |
| Volume (cm$^3$) per 1 mol of Na | 20.9 | 27.4 | 30.7 | 36.9 |

It is understood from the above findings that caking can be prevented by preventing the change on the surface of the sodium hydrogencarbonate crystal particles and making the composition on the surface of the sodium hydrogencarbonate crystal particles be stable crystals in the storage atmosphere. However, the environment for storage of sodium hydrogencarbonate varies depending upon the seasonal factor, etc., caking can not be prevented even when the surface of the sodium hydrogencarbonate crystal particles is fixed to have a certain crystal composition of only sodium carbonate monohydrate, only Wegscheider's salt or only sodium sesquicarbonate, as one example is shown below. According to experiments by the present inventors, in the air ($CO_2$ concentration 0.04 vol %), the boundary between Wegscheider's salt and sodium sesquicarbonate is as shown in the following Table 2, and stable crystals vary with the temperature and the humidity. The boundary between Wegscheider's salt and sodium sesquicarbonate also depends on the concentration of the carbon dioxide gas, and the boundary shifts toward a high humidity side as the carbon dioxide gas concentration increases. In a case where sodium hydrogencarbonate is hermetically sealed in e.g. a polyethylene bag, the carbon dioxide gas concentration in the bag increases to 0.1 vol % in some cases, and accordingly the boundary is present in a range of a relative humidity of from 35 to 50% depending upon the carbon dioxide concentration. With respect to the state of the sodium hydrogencarbonate crystal particles under weather conditions at a high humidity side and a low humidity side of the boundary, for example, in the rainy season, sodium sesquicarbonate is stable under a high humidity condition, and when the humidity is low, Wegscheider's salt is stable. Further, the relative humidity in the bag in which sodium hydrogencarbonate is packaged increases or decreases depending upon the difference in temperature between day and night. Thus, prevention of caking is hardly achieved only by bringing the surface of crystal particles of sodium hydrogencarbonate to have a predetermined composition of only Wegscheider's salt, only sodium carbonate monohydrate or only sodium sesquicarbonate.

TABLE 2

|  | Temperature (° C.) | | | | |
|---|---|---|---|---|---|
|  | 18 | 22 | 26 | 30 | 34 |
| Lowest relative humidity at which sodium sesquicarbonate is formed (%) | 37 | 36 | 35 | 34 | 33 |

However, the present inventors have noted a fact that caking is relatively weak when anhydrous sodium carbonate is converted into sodium carbonate monohydrate or Wegscheider's salt, but it is strong when anhydrous sodium carbonate is converted into sodium sesquicarbonate, a fact that a predetermined humidity as shown in Table 2 is required when anhydrous sodium carbonate, sodium carbonate monohydrate or Wegscheider's salt is converted into sodium sesquicarbonate, and a fact that sodium hydrogencarbonate crystal particles are usually contained and stored as packaged in an enclosed space such as in a polyethylene packaging bag. Further, they have found that caking of sodium hydrogencarbonate crystal particles can be prevented within a substantially tolerable range over a long period of time by making anhydrous sodium carbonate in an amount within a specific range and sodium carbonate monohydrate and/or Wegscheider's salt converted from the anhydrous sodium carbonate in a specific amount be present on the surface of sodium hydrogencarbonate crystal particles.

Here, in the present invention, the present inventors suppose that for example, when anhydrous sodium carbonate absorbs moisture e.g. by humidification to form sodium carbonate monohydrate or Wegscheider's salt, the most part of the outermost layer on the surface of the sodium carbonate crystal particles comprises sodium carbonate monohydrate or Wegscheider's salt. When expressing and explaining schematically, the surface of the sodium hydrogencarbonate crystal particles comprises anhydrous sodium carbonate, and sodium carbonate monohydrate or Wegscheider's salt, and the outermost layer on the surface of the crystal particles contains sodium carbonate monohydrate or Wegscheider's salt in a large amount. And, the crystal particles of sodium hydrogencarbonate are in contact with one another at the outermost layer containing sodium carbonate monohydrate or Wegscheider's salt in a large amount.

The function of anhydrous sodium carbonate in such a state of crystal particles is described first. In a case where anhydrous sodium carbonate in a specific amount, and sodium carbonate monohydrate or Wegscheider's salt converted from the anhydrous sodium carbonate in a specific amount, are made to be present on the surface of sodium hydrogencarbonate crystal particles, and the crystal particles are stored as packaged in an enclosed space, anhydrous sodium carbonate on the surface functions as a kind of a drying agent to absorb moisture in the packaging space and is converted into sodium carbonate monohydrate or Wegscheider's salt. And so long as anhydrous sodium carbonate is present, conversion of anhydrous sodium carbonate into sodium carbonate monohydrate or Wegscheider's salt continuously proceeds, whereby the humidity in the packaging space can be maintained low. Therefore, no humidity required to cause conversion from anhydrous sodium carbonate into sodium sesquicarbonate via sodium carbonate monohydrate or Wegscheider's salt, resulting in strong caking, is provided. Resultingly, the most part of the outermost layer on the surface at which the sodium hydrogencarbonate crystal particles are in contact with one another, remains to comprise sodium carbonate monohydrate or Wegscheider's salt, whereby crosslinking among crystal particles resulting from conversion into sodium sesquicarbonate hardly occurs. Thus, caking of the sodium hydrogencarbonate crystal particles is prevented in a substantially tolerable range.

Further, for comparison, an explanation is made with reference to a case where the outer layer of the sodium hydrogencarbonate crystal particles comprises only anhydrous sodium carbonate. By the moisture-absorbing function of anhydrous sodium carbonate, a packaged product of sodium hydrogencarbonate crystal particles is maintained in a low humidity atmosphere, and occurrence of caking is suppressed. However, anhydrous sodium carbonate is eventually converted into sodium carbonate monohydrate or Wegscheider's salt, and accordingly weak caking is likely to occur in the case of only anhydrous sodium carbonate as compared with the present invention. If it is attempted to increase the moisture-absorbing function of anhydrous sodium carbonate, the content of anhydrous sodium carbonate has to be high, and accordingly the degree of the weak caking tends to increase and will exceed the tolerable range at last.

As mentioned above, according to the present invention, sodium hydrogencarbonate crystal particles having a higher anticaking property imparted can be provided by a totally novel idea that anhydrous sodium carbonate is present as a drying agent, the presence of which has been avoided, on the sodium hydrogencarbonate crystal particles, and part of anhydrous sodium carbonate is converted into sodium carbonate monohydrate or Wegscheider's salt which coexists with anhydrous sodium carbonate, so as to suppress occurrence of caking even if the content of anhydrous sodium carbonate is increased.

Here, whether anhydrous sodium carbonate is converted into sodium carbonate monohydrate or Wegscheider's salt is determined by the temperature, the humidity or the carbon dioxide gas concentration. When the temperature is not high and the carbon dioxide gas concentration and the relative humidity are low, Wegscheider's salt is likely to form. In order to know which crystals will be formed, anhydrous sodium carbonate is preliminarily stored under the corresponding conditions, followed by structural analysis of crystals e.g. by X-ray diffraction or by confirmation by a phase equilibrium diagram.

Namely, the present invention provides the following.

(1) Sodium hydrogencarbonate crystal particles having a low caking property, which comprise sodium hydrogencarbonate crystal particles having an average particle size of from 50 to 500 μm based on the mass, and anhydrous sodium carbonate, and sodium carbonate monohydrate and/or Wegscheider's salt, present on the surface of the sodium hydrogencarbonate crystal particles in such amounts that the total content of anhydrous sodium carbonate, sodium carbonate monohydrate, Wegscheider's salt and sodium sesquicarbonate in the sodium hydrogencarbonate crystal particles is from 0.04 to 1 mass % as calculated as anhydrous sodium carbonate, anhydrous sodium carbonate accounts for at least 40 mass % of the total content, and sodium carbonate monohydrate and/or Wegscheider's salt accounts for from 5 to 60 mass % of the total content.

(2) The sodium hydrogencarbonate crystal particles having a low caking property according to the above (1), wherein the total content of anhydrous sodium carbonate, sodium carbonate monohydrate, Wegscheider's salt and sodium sesquicarbonate in the sodium hydrogencarbonate crystal particles is from 0.1 to 0.9 mass % as calculated as anhydrous sodium carbonate, anhydrous sodium carbonate accounts for at least 40 mass % of the total content, and sodium carbonate monohydrate and/or Wegscheider's salt accounts for from 5 to 60 mass % of the total content.

(3) A process for producing the sodium hydrogencarbonate crystal particles having a low caking property as defined in the above (1) or (2), which comprises subjecting sodium hydrogencarbonate crystal particles to heat treatment to convert part of the sodium hydrogencarbonate crystal particles into anhydrous sodium carbonate, followed by humidification to convert part of anhydrous sodium carbonate into sodium carbonate monohydrate and/or Wegscheider's salt.

(4) The production process according to the above (3), wherein a slurry containing sodium hydrogencarbonate is obtained by crystallization, wet sodium hydrogencarbonate crystal particles are separated from the slurry, and the wet sodium hydrogencarbonate crystal particles are subjected to heat treatment.

(5) A method of packaging sodium hydrogencarbonate crystal particles, which comprises packaging the sodium hydrogencarbonate crystal particles as defined in the above (1) or (2) or obtained by the production process as defined in the above (3) or (4), in a material having a water vapor transmission rate of at most 5 g/(m$^2$·24 h) at 40° C. with a relative humidity difference of 90% as stipulated in JIS K 7129.

(6) The packaging method according to the above (5), wherein the material for packaging is a laminated sheet using a resin sheet obtained by vapor deposition treatment with alumina or silica.

(7) The packaging method according to the above (6), wherein the innermost layer of the laminated sheet as the material for packaging, to be in contact with the sodium hydrogencarbonate crystal particles, is made of an additive-free polyethylene.

EFFECTS OF THE INVENTION

According to the present invention, by a novel idea that anhydrous sodium carbonate in an amount within a specific range, and sodium carbonate monohydrate and/or Wegscheider's salt in an amount within a specific range, are made to be present on the surface of sodium hydrogencarbonate crystal particles, caking on the surface of the sodium hydrogencarbonate crystal particles can be reduced within a tolerable range over a long period of time without use of an anticaking agent. As a result, sodium hydrogencarbonate crystal particles having a low caking property, which require no selection of the type of the anticaking agent, the use of which is not limited, which do not require a long treatment time, and which are suitably applicable to industrial fields such as food products, pharmaceuticals, bath additives, etc., can be obtained.

Further, according to the present invention, it is possible to prevent caking over a long period of time by packaging the obtained sodium hydrogencarbonate crystal particles having a low caking property in a packaging material having a vapor transmission or below.

BEST MODE FOR CARRYING OUT THE INVENTION

The sodium hydrogencarbonate crystal particles having a low caking property of the present invention may have any average particle size, but have an average particles size of from 50 to 500 μm, preferably from 70 to 300 μm. If the average particle size exceeds 500 μm, the influence of the mass of the crystal particles tends to be significant, and caking is likely to disintegrate by the gravity. Further, if it is smaller than 50 μm, particles tend to agglomerate by the influence of the force between particles such as Van der Waals force, and the number of sites at which the particles are in contact with one another per unit volume of the particles tends to increase, whereby the crystal particles inherently tend to be caked. Here, the average particle size is an average particle size based on the mass, and is defined as the 50% particle size in the cumulative particle size distribution based on the mass obtained by a sieving method. Specifically, measurement is carried out by means of a Ro-Tap shaker and a sieving method (hereinafter referred to simply as a sieving method) as stipulated in JIS Z 8801-1.

The sodium hydrogencarbonate crystal particles to be subjected to heat treatment in the present invention may be sodium hydrogencarbonate crystal particles in a wet state separated from a slurry containing sodium hydrogencarbonate in the existing process for producing sodium hydrogencarbonate crystal particles or may be sodium hydrogencarbonate crystal particles which have already been produced. For example, they may be (i) sodium hydrogencarbonate crystal particles in a wet state separated from a slurry containing sodium hydrogencarbonate obtained in a crystallization step of reacting an aqueous sodium carbonate solution or an aqueous sodium carbonate solution containing sodium hydroxide or sodium hydrogencarbonate with a carbon dioxide gas to obtain sodium hydrogencarbonate, may be (ii) sodium hydrogencarbonate crystal particles obtained by drying the sodium hydrogencarbonate crystal particles in a wet state, may be (iii) sodium hydrogencarbonate crystal particles obtained by sieving the dried sodium hydrogencarbonate crystal particles, or may be (iv) sodium hydrogencarbonate crystal particles obtained by pulverizing and classifying the sieved sodium hydrogencarbonate crystal particles. In the case of the above (i), a drying step and a step of forming anhydrous sodium carbonate do not have to be carried out separately when heating treatment is conducted so as to function also as drying the sodium hydrogencarbonate crystal particles, such being efficient from an economical viewpoint also. In the case where an additional equipment is provided with the existing equipment to carry out the present invention, a proper method may be selected from the above methods depending upon circumstances such that the scale of the additional equipment should be small.

On the surface of the sodium hydrogencarbonate crystal particles having a low caking property of the present invention, anhydrous sodium carbonate in an amount within a specific range, and sodium carbonate monohydrate and/or Wegscheider's salt converted from the anhydrous sodium carbonate in an amount within a specific range, are present. Here, the surface of the sodium hydrogencarbonate crystal particles means the surface of the crystal particles, and a portion preferably within about 5 μm, particularly preferably within about 2 μm below the surface. In the present invention, presence of anhydrous sodium carbonate and sodium carbonate monohydrate and/or Wegscheider's salt each in a predetermined amount on the surface of the sodium hydrogencarbonate crystal particles is essential, and it is required that the total content of anhydrous sodium carbonate, sodium carbonate monohydrate, Wegscheider's salt and sodium sesquicarbonate in the sodium hydrogencarbonate crystal particles is from 0.04 to 1 mass % as calculated as anhydrous sodium carbonate, anhydrous sodium carbonate accounts for at least 40 mass % of the total content, and sodium carbonate monohydrate and/or Wegscheider's salt accounts for from 5 to 60 mass % of the total content. Here, the mass of the sodium hydrogencarbonate crystal particles as the basis is the mass of the crystal particles themselves and is not calculated as anhydrous sodium carbonate.

If the above total content of anhydrous sodium carbonate, sodium carbonate monohydrate, Wegscheider's salt and sodium sesquicarbonate is less than 0.04 mass %, the effect of preventing caking according to the present invention tends to be insufficient. On the other hand, if it exceeds 1 mass %, the effect of preventing caking will be achieved, but the purity of sodium hydrogencarbonate as a product i.e. the content of sodium hydrogencarbonate tends to decrease, such being unfavorable. The above total content is preferably from 0.05 to 0.9 mass %, particularly preferably from 0.1 to 0.9 mass %.

Further, if the amount of anhydrous sodium carbonate present is less than 40 mass % of the total content of anhydrous sodium carbonate, sodium carbonate monohydrate, Wegscheider's salt and sodium sesquicarbonate, since the content of anhydrous sodium carbonate which functions as a drying agent tends to be low, the persistence of the effect of preventing caking tends to decrease, and the caking-preventing property over a long period of time will be lost. The amount of anhydrous sodium carbonate present is more preferably at least 50 mass %, more preferably at least 60 mass % of the above total content.

If the amount of sodium carbonate monohydrate and/or Wegscheider's salt present is less than 5 mass % of the total content of anhydrous sodium carbonate, sodium carbonate monohydrate, Wegscheider's salt and sodium sesquicarbonate, a large portion on the surface of the sodium hydrogencarbonate crystal particles tends to have a composition other than sodium carbonate monohydrate and/or Wegscheider's salt, and initial caking is likely to occur, resulting from conversion of anhydrous sodium carbonate into sodium carbonate monohydrate or Wegscheider's salt. On the other hand, if it exceeds 60 mass % of the total content, the content of anhydrous sodium carbonate which functions as a drying agent tends to be too low, such being unfavorable. The amount of sodium carbonate monohydrate and/or Wegscheider's salt present is more preferably at least 10 mass %, furthermore preferably at least 20 mass %, and more preferably at most 50 mass %, furthermore preferably at most 40 mass %. Here, the above composition of the surface of the sodium hydrogencarbonate crystal particles of the present invention represents the state at the time of at least production and delivery of the sodium hydrogencarbonate crystal particles, and this surface state is preferably maintained until the sodium hydrogencarbonate crystal particles are used. If the crystal particles are packaged in a material having a low vapor transmission as disclosed in the present invention, the effect will be maintained for a longer period of time.

The sodium hydrogencarbonate crystal particles of the present invention, on the surface of which anhydrous sodium carbonate, and sodium carbonate monohydrate and/or Wegscheider's salt are present, are produced efficiently in a short time by applying heat treatment to the surface of sodium hydrogencarbonate crystal particles to form anhydrous sodium carbonate, followed by humidification. Namely, in the present invention, sodium hydrogencarbonate crystal particles are subjected to heat treatment so that the surface of the sodium hydrogencarbonate crystal particles is decomposed to form anhydrous sodium carbonate, and then part of the formed anhydrous sodium carbonate is humidified to form sodium carbonate monohydrate and/or Wegscheider's salt. Formation of anhydrous sodium carbonate by heating the surface of the sodium hydrogencarbonate crystal particles and formation of sodium carbonate monohydrate or Wegscheider's salt by humidifying the anhydrous sodium carbonate thus formed, can be achieved easily by a treatment in a short time as compared with formation of sodium sesquicarbonate on the surface of the sodium hydrogencarbonate crystal particles. The process comprising the step of decomposing the sodium hydrogencarbonate crystal particles of the present invention is very different from a conventional production process with careful attention not to decompose sodium hydrogencarbonate at all, such as a process which comprises a drying step requiring heating, wherein for the drying step, a heated carbon dioxide gas is used so that sodium hydrogencarbonate will not be decomposed as far as possible ("Soda handbook", page 105 (published by Japan Soda Industry Association in 1975)). Further, even when the air is used for drying, the idea of the present invention is exactly opposite to a process of the above-described Japanese Patent No. 3306873 (20 to 60° C.) or a process of the above-described "MANUFACTURE OF SODA", page 282 (40 to 50° C.), in which it is attempted not to raise the temperature of sodium hydrogencarbonate as far as possible.

In the present invention, as a means of subjecting the sodium hydrogencarbonate crystal particles to heat treatment to form anhydrous sodium carbonate on the surface of the sodium hydrogencarbonate crystal particles, it is preferred to bring the sodium hydrogencarbonate crystal particles into contact with a heated gas while they are made to flow, a rotary dryer or a fluidized bed may be suitable used. Particularly, preferred is a rotary dryer capable of providing a long retention time, capable of stably setting operation conditions in detail and capable of providing a flow close to the piston flow and thereby capable of uniform treatment. As the gas for heat treatment, the air or a nitrogen gas may be used, or a dry gas may be used in a recycling manner.

In the case where the sodium hydrogencarbonate is crystal particles are subjected to heat treatment to form anhydrous sodium carbonate on the surface of the particles, Wegscheider's salt, sodium carbonate monohydrate, sodium sesquicarbonate or sodium carbonate decahydrate may be formed as a by-product depending upon conditions such as the temperature, the humidity and the carbon dioxide gas concentration. However, in the present invention, the formation can be efficiently carried out preferably under the following conditions.

In the present invention, the gas used for the heat treatment suitably has a relative humidity of preferably at most 30%, more preferably at most 20%, particularly preferably at most 15%. The relative humidity is preferably as low as possible, since formation of Wegscheider's salt can be avoided even when the carbon dioxide gas concentration is high, and formation of sodium carbonate monohydrate, sodium sesquicarbonate or sodium carbonate decahydrate can be securely avoided. Here, the relative humidity is a value as calculated as the temperature of the sodium hydrogencarbonate crystal particles under the heat treatment.

Further, the temperature of the sodium hydrogencarbonate crystal particles in the heat treatment is preferably from 70 to 100° C., particularly preferably from 70 to 95° C. The treatment time tends to be longer when the temperature is lower, and accordingly if the temperature is less than 70° C., the retention time for the treatment tends to be long, and the equipment tends to be large. On the other hand, if the temperature is high, decomposition of the sodium hydrogencarbonate crystal particles tends to be accelerated, whereby it will be difficult to control the treatment operation, and anhydrous sodium carbonate at a predetermined concentration will hardly be achieved.

As specific preferred conditions to carry out the above heat treatment, the following conditions may be mentioned.

a. In a case where the relative humidity of the gas to be used for the heat treatment is within a range of at most 30% and higher than 20%, the carbon dioxide gas concentration of the gas to be used for the heat treatment is at most 3 vol % in a case where the temperature of the crystal particles of sodium hydrogencarbonate is 70° C., at most 4 vol % in the case of higher than 70° C. to 75° C., at most 7 vol % in the case of higher than 75° C. to 80° C., at most 11 vol % in the case of higher than 80° C. to 85° C., at most 19 vol % in the case of higher than 85° C. to 90° C., and at most 31 vol % in the case of higher than 90° C. to 95° C. More preferably, the carbon dioxide gas concentration is at most 2 vol % in a case where the temperature is 70° C., at most 3 vol % in the case of higher than 70° C. to 75° C., at most 5 vol % in the case of higher than 75° C. to 80° C., at most 9 vol % in the case of higher than 80° C. to 85° C., at most 15 vol % in the case of higher than 85° C. to 90° C., and at most 25 vol % in the case of higher than 90° C. to 95° C. Furthermore preferably, the carbon dioxide gas concentration is at most 1 vol % in a case where the temperature is 70° C., at most 2 vol % in the case of higher than 70° C. to 75° C., at most 4 vol % in the case of higher than 75° C. to 80° C., at most 6 vol % in the case of higher than 80° C. to 85° C., at most 11 vol % in the case of higher than 85° C. to 90° C., and at most 17 vol % in the case of higher than 90° C. to 95° C.

b. In a case where the relative humidity of the gas to be used for the heat treatment is within a range of at most 20% and higher than 10%, the carbon dioxide gas concentration of the gas to be used for the heat treatment is at most 4 vol % in a case where the temperature of the crystal particles of sodium hydrogencarbonate is 70° C., at most 6 vol % in the case of higher than 70° C. to 75° C., at most 11 vol % in the case of higher than 75° C. to 80° C., at most 17 vol % in the case of higher than 80° C. to 85° C., at most 29 vol % in the case of higher than 85° C. to 90° C., and at most 46 vol % in the case of higher than 90° C. to 95° C. More preferably, the carbon dioxide gas concentration is at most 3 vol % in a case where the temperature is 70° C., at most 5 vol % in the case of higher than 70° C. to 75° C., at most 9 vol % in the case of higher than 75° C. to 80° C., at most 15 vol % in the case of higher than 80° C. to 85° C., at most 25 vol % in the case of higher than 85° C. to 90° C., and at most 40 vol % in the case of higher than 90° C. to 95° C. Furthermore preferably, the carbon dioxide gas concentration is at most 2 vol % in a case where the temperature is 70° C., at most 3 vol % in the case of higher than 70° C. to 75° C., at most 6 vol % in the case of higher than 75° C. to 80° C., at most 10 vol % in the case of higher than 80° C. to 85° C., at most 16 vol % in the case of higher than 85° C. to 90° C., and at most 26 vol % in the case of higher than 90° C. to 95° C.

c. In a case where the relative humidity of the gas to be used for the heat treatment is within a range of at most 10% and higher than 5%, the carbon dioxide gas concentration of the gas to be used for the heat treatment is at most 8 vol % in a case where the temperature of the crystal particles of sodium hydrogencarbonate is 70° C., at most 13 vol % in the case of higher than 70° C. to 75° C., at most 21 vol % in the case of higher than 75° C. to 80° C., at most 34 vol % in the case of higher than 80° C. to 85° C., at most 57 vol % in the case of higher than 85° C. to 90° C., and at most 100 vol % in the case of higher than 90° C. to 95° C. More preferably, the carbon dioxide gas concentration is at most 6 vol % in a case where the temperature is 70° C., at most 11 vol % in the case of higher than 70° C. to 75° C., at most 19 vol % in the case of higher than 75° C. to 80° C., at most 30 vol % in the case of higher than 80° C. to 85° C., at most 52 vol % in the case of higher than 85° C. to 90° C., and at most 90 vol % in the case of higher than 90° C. to 95° C. Furthermore preferably, the carbon dioxide gas concentration is at most 5 vol % in a case where the temperature is 70° C., at most 7 vol % in the case of higher than 70° C. to 75° C., at most 12 vol % in the case of higher than 75° C. to 80° C., at most 19 vol % in the case of higher than 80° C. to 85° C., at most 32 vol % in the case of higher than 90° C. to 90° C., and at most 56 vol % in the case of higher than 90° C. to 95° C.

d. In a case where the relative humidity of the gas to be used for the heat treatment is within a range of at most 5%, the carbon dioxide gas concentration of the gas to be used for the heat treatment is at most 16 vol % in a case where the temperature of the crystal particles of sodium hydrogencarbonate is 70° C., at most 25 vol % in the case of higher than 70° C. to 75° C., at most 45 vol % in the case of higher than 75° C. to 80° C., at most 73 vol % in the case of higher than 80° C. to 85° C., at most 100 vol % in the case of higher than 85° C. to 90° C., and at most 100 vol % in the case of higher than 90° C. to 95° C. More preferably, the carbon dioxide gas concentration is at most 14 vol % in a case where the temperature is 70° C., at most 23 vol % in the case of higher than 70° C. to 75° C., at most 40 vol % in the case of higher than 75° C. to 80° C., at most 68 vol % in the case of higher than 80° C. to 85° C., at most 90 vol % in the case of higher than 85° C. to 90° C., and at most 90 vol % in the case of higher than 90° C. to 95° C. Furthermore preferably, the carbon dioxide gas concentration is at most 9 vol % in a case where the temperature is 70° C., at most 14 vol % in the case of higher than 70° C. to 75° C., at most 25 vol % in the case of higher than 75° C. to 80° C., at most 41 vol % in the case of higher than 80° C. to 85° C., at most 57 vol % in the case of higher than 85° C. to 90° C., and at most 60 vol % in the case of higher than 90° C. to 95° C.

In such a manner, sodium hydrogencarbonate on the surface of the sodium hydrogencarbonate crystal particles is decomposed into anhydrous sodium carbonate, and on the surface of the sodium hydrogencarbonate crystal particles, anhydrous sodium carbonate is formed. Then, as a method of humidifying anhydrous sodium carbonate formed on the surface of the sodium hydrogencarbonate crystal particles to convert it into sodium carbonate monohydrate and/or Wegscheider's salt, preferred is to bring a humidified gas (hereinafter referred to simply as a humid gas) and the sodium hydrogencarbonate crystal particles containing anhydrous sodium carbonate into contact with each other. In the humid gas, the composition other than moisture is not particularly limited so long as it comprises a gas which will not chemically react with sodium hydrogencarbonate, anhydrous sodium carbonate, sodium carbonate monohydrate, Wegscheider's salt and sodium sesquicarbonate, but the air or a nitrogen gas is preferably used in view of handling efficiency. The humid air, which can be simply used, is particularly preferred. Further, such a humid gas may be used in a recycling manner.

In the humid gas such as the humid air or a humid nitrogen gas, the concentration of the carbon dioxide gas is preferably low. If the carbon dioxide concentration is high, a region of sodium hydrogencarbonate is achieved under a low temperature condition, and accordingly the temperature should be increased so as to achieve a region of sodium carbonate monohydrate or Wegscheider's salt. In such a case, treatment operation tends to be difficult. Accordingly, the carbon dioxide gas concentration is required to be at most 20 vol %. It is preferably at most 10 vol %, more preferably at most 5 vol %. When the humid gas is used in a recycling manner, the concentration of the carbon dioxide gas formed by decomposition of sodium hydrogencarbonate tends to increase, and accordingly it is required to carefully control the concentration of the carbon dioxide gas.

The following Table 3 illustrates the relative humidity at which anhydrous sodium carbonate is converted into sodium carbonate monohydrate or Wegscheider's salt. The humidity of the humid gas is preferably the relative humidity at which the region of sodium carbonate monohydrate or Wegscheider's salt is achieved as shown in Table 3. Therefore, the lower limit of the relative humidity of the air for humidification is the value shown in Table 3. Here, the air is employed, but the gas may not be the air so long as it is a gas which will not react with anhydrous sodium carbonate since the water vapor partial pressure is an operational factor at the time of humidification. For example, a nitrogen gas may be employed under the same operational conditions. That is, the relative humidity of the humid gas is at least 1% at a temperature of 25° C., at least 3% at a temperature of 30° C., at least 10% at a temperature of 40° C., and so on. On the other hand, as the upper limit of the humidity of the humid gas, the relative humidity is 95%. If the relative humidity is at least 95%, condensation is likely to occur at a part of the humidification equipment. Otherwise, sodium carbonate decahydrate may form under a low temperature condition. Further, the temperature of the sodium hydrogencarbonate crystal particles at the time of humidification treatment is from 25 to 90° C. If it is less than 25° C., the humidification treatment tends to take long. It is more preferably at least 30° C., more preferably at least 40° C. If the temperature exceeds 90° C., sodium hydrogencarbonate is likely to decompose, such being unfavorable, and the temperature is more preferably at most 80° C.

TABLE 3

Relative humidity of the air at which anhydrous sodium carbonate is converted into sodium carbonate monohydrate or Wegscheider's salt

| | Temperature (° C.) | | | | | | | |
|---|---|---|---|---|---|---|---|---|
| | 25 | 30 | 40 | 50 | 60 | 70 | 80 | 90 |
| Relative humidity (%) | 1 | 3 | 10 | 30 | 41 | 49 | 58 | 68 |

As a humidification apparatus to convert anhydrous sodium carbonate into sodium carbonate monohydrate or Wegscheider's salt, it is preferred to bring the sodium hydrogencarbonate crystal particles on the surface of which anhydrous sodium carbonate is formed, into contact with the humid gas while they are made to flow, and a method of humidifying the sodium hydrogencarbonate crystal particles with stirring employing a fluidized bed, a rotating cylinder apparatus, a paddle mixer or the like, may be suitably employed. Particularly preferred is a rotating cylinder apparatus or a paddle mixer capable of providing a long retention time, capable of stably setting operation conditions in detail, and capable of providing a flow close to the piston flow and thereby capable of uniform treatment.

The sodium hydrogencarbonate crystal particles of the present invention thus obtained, having anhydrous sodium carbonate in an amount within a specific range, and sodium carbonate monohydrate and/or Wegscheider's salt in an amount within a specific range on their surface, are usually packaged, delivered and transported, and stored by a distributor or a user. In the present invention, when the obtained sodium hydrogencarbonate crystal particles are packaged, it is suitable to use, as a packaging material, a packaging material having a water vapor transmission rate of at most 5 g/(m$^2$·24 h), particularly preferably at most 1 g/(m$^2$·24 h), at 40° C. with a relative humidity difference of 90% as stipulated in JIS K 7129. By use of such a packaging material having a water vapor transmission rate within the above range, the surface state of the sodium hydrogencarbonate crystal particles having anhydrous sodium carbonate, and sodium carbonate monohydrate and/or Wegscheider's salt on their surface, at the time of production and delivery, will be maintained over a long period of time, and the persistence of the caking preventing performance will remarkably increase.

As the packaging material having the above water vapor transmission rate, for example, it is preferred to use a sheet or a film of a resin having alumina or silica vapor-deposited on its surface as a dampproof layer. As an example of the structure of such a packaging material, a laminated sheet may be preferably used, which is obtained in such a manner that a polyethylene terephthalate film (hereinafter referred to as a PET film) having a thickness of preferably from 5 to 30 μm, having alumina or silica vapor-deposited thereon, is used as a dampproof layer for the outermost layer so that the vapor deposition layer faces inside, and as the case requires, a biaxially oriented nylon film (hereinafter referred to as an ON film) having a thickness of preferably from 5 to 30 μm for improving penetration resistance is used for the interlayer, and for the innermost layer to be in contact with the sodium hydrogencarbonate crystal particles, a linear low density polyethylene film (hereinafter referred to as an LLDPE film) having a thickness of preferably from 30 to 150 μm is dry-laminated.

For the dampproof layer in the above laminated sheet, an aluminum thin membrane or an aluminum-vapor deposited film may also be used, but they are not transparent, and they may be a barrier in a metal-detecting step at the time of delivery. Further, for the dampproof layer, a vinylidene chloride-coated film may also be used, but since it contains chlorine, hydrogen chloride gas will be generated when a packaging bag is burned at the time of its disposal, such being unfavorable. In this regard, it is preferred to use the above PET film having alumina or silica vapor-deposited as a dampproof layer, which is transparent, which will pass through a metal detector, and which generates no hydrogen chloride at the time of burning. As a method of vapor-depositing alumina or silica, PVD (physical vapor deposition) method in addition to CVD (chemical vapor deposition) method may be used. As a substrate on which they are vapor-deposited, an ON film may also be used in addition to the PET film.

Further, since the LLDPE film for the innermost layer in the laminated sheet will be in direct contact with the sodium hydrogencarbonate crystal particles as a product, and it is preferred to use a completely additive-free LLDPE which contains no antioxidant or the like which may cause coloring of the product, etc. It is possible to use a low density polyethylene instead of LLDPE, but LLDPE is more preferred, which is excellent in heat-sealing strength.

EXAMPLES

Now, the present invention will be described in detail with Examples, but it should be understood that the present invention is by no means restricted to such specific Examples.

Example 1

Sodium hydrogencarbonate crystal particles (hereinafter referred to simply as products) having various surface compositions were produced under the following conditions. In Table 4, Nos. 1 to 3 and No. 6 correspond to Example of the present invention, and Nos. 4 and 5 correspond to Comparative Example.

20 $m^3$ of an aqueous sodium hydroxide solution having a concentration of 20 mass % was put in a tank (50 $m^3$) provided with a stirrer, and the temperature was raised to 80° C. In such a state, a carbon dioxide gas at a concentration of 100 vol % was blown for 5 hours in a flow rate of 10 $m^3$ per minute in a standard state for reaction crystallization. In the crystallization step, first, sodium hydroxide is reacted with carbon dioxide to form sodium carbonate. So far, no crystals are precipitated. is Then, carbon dioxide and sodium carbonate are reacted to form sodium hydrogencarbonate. Here, as the solubility of sodium hydrogencarbonate is low, crystal particles of sodium hydrogencarbonate are precipitated. Then, by decreasing the temperature to 40° C. while the carbon dioxide gas is continuously blown, the sodium hydrogencarbonate crystal particles were further precipitated. The obtained slurry was subjected to a centrifugal separator to separate the mother liquor, thereby to obtain wet sodium hydrogencarbonate crystal particles.

The wet crystal particles were brought into contact with a drying gas consisting of a carbon dioxide gas-containing air in a parallel flow manner under conditions as shown in the following Table 4 using a rotary dryer (manufactured by MASUNO SEISAKUSHO LTD.) so that the sodium hydrogencarbonate crystal particles were dried and part of the sodium hydrogencarbonate crystal particles were baked to form anhydrous sodium carbonate.

The obtained sodium hydrogencarbonate crystal particles contained 0.42 mass % of sodium carbonate and contained no sodium carbonate monohydrate, Wegscheider's salt nor sodium sesquicarbonate. These facts were confirmed by measuring methods as described hereinafter.

In Table 4, the temperature of the sodium hydrogencarbonate crystal particles discharged from the rotary dryer is represented as a drying temperature, and the relative humidity and the carbon dioxide gas concentration of the drying gas were values as calculated as the temperature of the sodium hydrogencarbonate crystal particles. In order to immediately humidify the sodium hydrogencarbonate crystal particles after drying, a cylindrical apparatus (hereinafter referred to simply as a paddle mixing apparatus) provided with a paddle mixer and a jacket capable of cooling by indirect heat exchange, which can blow a gas for humidification into the interior thereof, was provided immediately after the rotary dryer to cool the sodium hydrogencarbonate crystal particles to 30° C. while they were humidified. The gas blown to the paddle mixing apparatus to humidify the sodium hydrogencarbonate crystal particles containing anhydrous sodium carbonate discharged from the rotary dryer, was humid air. The carbon dioxide concentration of the humid air used was 0.04 vol %. The amount of the sodium hydrogencarbonate crystal particles treated was 4 t per hour, and the flow rate of the humid air was 100 $m^3$ per hour in a standard state.

In Table 4, the relative humidity of the humid air is represented by the relative humidity as calculated as the temperature of the sodium hydrogencarbonate crystal particles discharged from the paddle mixing apparatus, i.e. 30° C. Then, the sodium hydrogencarbonate crystal particles thus obtained were subjected to sieving by using a circular shaking sieve provided with an ultrasonic oscillator and provided with a mesh with an opening of 0.25 mm, and particles which passed through a sieve were obtained as a product. This product was employed for the following evaluation regarding the caking. The product which is particles which passed through the sieve has an average particle size of 0.1 mm.

An experiment was carried out wherein no humidification was carried out by the paddle mixing apparatus as a Comparative Example, and shown in No. 5 in Table 4. In this case, no humid air was blown to the paddle mixing apparatus, but a dry air having a dew point of −40° C. was heated at 20° C. and blown to a cooling device. The carbon dioxide gas concentration of the dry gas used was 0.04 vol %. In such a manner, a product, of which the anhydrous sodium carbonate layer did not absorb moisture, and which contained anhydrous sodium carbonate and contained no sodium carbonate monohydrate nor Wegscheider's salt, was obtained. The content of sodium carbonate in the sodium hydrogencarbonate crystal particles thus obtained was 0.42 mass % which was the same as that of the sodium hydrogencarbonate crystal particles discharged from the rotary dryer.

Then, a test method for evaluating the caking property of a product is specifically described below.

1 kg of the product of the sodium hydrogencarbonate crystal particles having an average particle size of 0.1 mm obtained as particles which passed through a sieve by using the above-described circular shaking sieve provided with an ultrasonic oscillator was weighed, and put in a bag made of completely additive-free LLDPE film having a thickness of 120 μm and hermetically sealed by heat sealing, which was left at rest for one month in an atmosphere at 25° C. at a relative humidity of 85%. After still standing, the bag was carefully opened so that the product would not disintegrate and delicately poured on a test sieve (hereinafter referred to simply as "sieve") having an inner diameter of 20 mm, having a wire netting with an opening of 3 mm set thereto, as stipulated in JIS Z 8801-1. The mass of the product and the sieve was weighed to measure the mass of the product on the sieve to determine the mass ratio to the entire product. The ratio was defined as the "amount of particles weakly caked". Here, the product which was caked as a whole at the time of opening is considered to have a ratio of 100%.

Then, the sieve on which the product was put was tapped with a hand for three seconds, and the mass of the product and the sieve was weighed to measure the mass of the product on the sieve, to determine the mass ratio to the product at the time of packaging. This ratio was defined as the "amount of particles moderately caked". Further, the sieve on which the product was put was tapped with a hand for 10 seconds, and mass of the product and the sieve was weighed to measure the mass of the product put on the sieve, to determine the mass ratio to the product at the time of packaging. This ratio was defined as the "amount of product strongly caked". The above test for evaluating the caking property will be referred to simply as a caking property evaluation test.

The average particle size of the product before the caking property evaluation test depends on the sieving method, and the opening of the sieve used was 355 μm, 250 μm, 180 μm, 150 μm, 106 μm, 75 μm or 45 μm.

Further, for measurement of anhydrous sodium carbonate, sodium carbonate monohydrate, Wegscheider's salt and sodium sesquicarbonate, the total amount of anhydrous sodium carbonate, sodium carbonate monohydrate and sodium sesquicarbonate in the product was quantitatively determinate by anhydrous methanol extraction method as described hereinafter, and the content of sodium carbonate monohydrate or Wegscheider's salt and the content of sodium sesquicarbonate in the product was determined by TGA method as described hereinafter. From the measurement results by these methods, the respective amount of anhydrous sodium carbonate, sodium carbonate monohydrate, Wegscheider's salt and sodium sesquicarbonate in the sodium hydrogencarbonate crystal particles were determined.

The anhydrous methanol extraction method will be described below.

In the present invention, the "anhydrous methanol extraction method" means a method wherein the total amount of anhydrous sodium carbonate, sodium carbonate monohydrate and sodium sesquicarbonate in the product is analyzed by extracting the respective components from sodium hydrogencarbonate with anhydrous methanol, followed by neutralization titration. Specifically, 5 g of the product is weighed, which is put in 100 mL of anhydrous methanol, followed by shaking for 30 minutes. Then, titration is carried out with 0.1 N hydrochloric acid with phenolphthalein as an indicator to quantatively determine the total amount of anhydrous sodium carbonate, sodium carbonate monohydrate and sodium sesquicarbonate in the product. Here, the 0.1 N hydrochloric acid is prepared by diluting a 35 mass % hydrochloric acid aqueous solution with anhydrous methanol so as to reduce inclusion of moisture as far as possible. Or, a methanol solution of hydrogen chloride may be used. Here, Wegscheider's salt is substantially insoluble in anhydrous methanol and is thereby not measured by the anhydrous methanol extraction method. Further, Wegscheider's salt will be formed if a sample to be subjected to measuring is left to stand at room temperature for long period of time and absorbs moisture, and accordingly analysis should be carried out quickly after sampling.

Now, the TGA method will be explained below.

In the present invention, the "TGA method" is a method of measuring the contents of sodium carbonate monohydrate, Wegscheider's salt and sodium sesquicarbonate in the sodium hydrogencarbonate crystal particles, and is a method of measuring the mass reduction of the respective components by thermolysis at specific two levels of temperatures by a thermogravimetric analyzer and analyzing the content of a sodium carbonate monohydrate or Wegscheider's salt component and the content of a sodium sesquicarbonate component from the difference in the weight reduction profile between the two levels of temperatures.

A certain amount of the present product as a sample to be measured is put in a sample cell, and the product is heated at a constant temperature in a drying gas such as a nitrogen gas, which will not react with sodium hydrogencarbonate, anhydrous sodium carbonate, sodium carbonate monohydrate, Wegscheider's salt nor sodium sesquicarbonate, and the mass reduction when sodium carbonate monohydrate, Wegscheider's salt and sodium sesquicarbonate are decomposed into anhydrous sodium carbonate is precisely measured.

Specifically, a predetermined amount of the product is weighed in a sample cell, and measurement is carried out at a predetermined temperature by an isothermal method using a nitrogen gas containing substantially no moisture by means of a thermogravimetric analyzer. Here, the measurement can be carried out utilizing the facts is newly found by the present inventors that sodium hydrogencarbonate is more thermal stable and is less likely to decompose than sodium carbonate monohydrate, Wegscheider's salt and sodium sesquicarbonate and that sodium sesquicarbonate is more thermally stable than sodium carbonate monohydrate and Wegscheider's salt. Namely, employing two levels of predetermined measurement temperatures, and from the difference, the content of sodium carbonate monohydrate or Wegscheider's salt and the content of sodium sesquicarbonate can be accurately determined. For the lower temperature between the two levels of the temperatures, such a temperature is selected that decomposition of sodium carbonate monohydrate or Wegscheider's salt is substantially completed in a certain time and decomposition of sodium sesquicarbonate does not substantially start. Further, for the higher temperature, such a temperature is selected that decomposition of sodium carbonate monohydrate, Wegscheider's salt and sodium sesquicarbonate is substantially completed in a certain time. The temperature and the time vary in accordance with the amount of the sample for measurement, the structure of the measuring apparatus, the structure of the sample container, etc.

The absolute value of sodium carbonate monohydrate or Wegscheider's salt and the absolute value of sodium sesquicarbonate are determined based on the standard additional sample comprising particles of each component added to sodium hydrogencarbonate crystal particles containing no sodium carbonate monohydrate, Wegscheider's salt nor sodium sesquicarbonate.

In the present Example, thermo-gravimetric/differential thermal analyzer TG/DTA6200 manufactured by SII Nanotechnology Inc. was used. In this measurement, the lower temperature was 53° C., the higher temperature was 63° C., and the weight reduction after a lapse of 50 minutes was measured at each temperature. The amount of the sample used for the measurement was 60 mg. Further, to correct the weight reduction by decomposition of sodium hydrogencarbonate itself in a certain time at each of the two levels of temperatures, measurement was separately carried out with respect to sodium hydrogencarbonate containing substantially no sodium carbonate monohydrate, Wegscheider's salt and sodium sesquicarbonate, and the obtained weight reduction is subtracted from each measured value as a base line. The weight reduction at 53° C. corresponds to the content of sodium carbonate monohydrate or Wegscheider's salt, and the value obtained by subtracting the weight reduction at 53° C. from the weight reduction at 63° C. corresponds to the content of sodium sesquicarbonate. Sodium carbonate monohydrate and Wegscheider's salt were distinguished by judging which of the region of sodium carbonate monohydrate or the region of Wegscheider's salt was achieved in a phase equilibrium diagram based on conditions of the temperature, the relative humidity and the carbon dioxide gas concentration under which the humidification treatment was carried out. In a case of not depending upon the phase equilibrium diagram, crystal particles of anhydrous sodium carbonate are stored in a long period of time under the atmosphere, and the change of the crystal is examined by structure analysis of the crystals by X-ray diffraction. Here, if the sample to be subjected to measurement by the TGA method is left to stand at room temperature for a long period of time, it will absorb moisture and thereby form Wegscheider's salt, and accordingly analysis should be carried out quickly after sampling.

The value obtained by subtracting the contents of sodium carbonate monohydrate and sodium sesquicarbonate determined by the TGA method from the content corresponding to the total amount of anhydrous sodium carbonate, sodium carbonate monohydrate and sodium sesquicarbonate determined by the anhydrous methanol extraction method, is the content of anhydrous sodium carbonate. If there is no mass reduction by pyrolysis of sodium carbonate monohydrate, Wegscheider's salt and sodium sesquicarbonate in the TGA method, the value determined by the anhydrous methanol extraction method all corresponds to the content of anhydrous sodium carbonate. The sodium hydrogencarbonate crystal particles before the humidification operation shown in Table 4 and Comparative Example No. 5 correspond to such a case.

The humidification conditions in Nos. 1 to 4 and No. 6 correspond to a region where Wegscheider's salt is to be formed. Further, as confirmed by the TGA method, no sodium sesquicarbonate is contained. Accordingly, the measured value determined by the anhydrous methanol extraction method corresponds to the content of anhydrous sodium carbonate as it is, and the value of Wegscheider's salt is a measured value determined by the TGA method.

In Table 4, the respective measured values are shown. Each content is calculated as anhydrous sodium carbonate. It is evident from Table 4, it is understood that the amount of particles moderately caked and the amount of particles strongly caked, including the amount of particles weakly caked estimated to result from initial caking, remarkably reduced by converting part of sodium hydrogencarbonate crystal particles into anhydrous sodium carbonate, followed by humidification to convert part of anhydrous sodium carbonate to Wegscheider's salt. Particularly when anhydrous sodium carbonate accounts for at least 40 mass % of the total content of anhydrous sodium carbonate, sodium carbonate monohydrate, Wegscheider's salt and sodium sesquicarbonate, the amount of particles caked is reduced. In the present Example, a case where Wegscheider's salt is formed is illustrated, but the same applies to sodium carbonate monohydrate.

Further, in the present Example, the humidification time is within 1 hour, which is shorter than when the surface layer of the product is made to comprise sodium sesquicarbonate. In order that the surface layer of a product comprises sodium sesquicarbonate, a higher humidity will be required, a carbon dioxide gas concentration must be adjusted and a longer time will be required.

TABLE 4

| | No. | | | | |
|---|---|---|---|---|---|
| | 1 | 2 | 3 | 4 | 5 |
| Drying temperature (° C.) | 90 | 90 | 90 | 90 | 90 |
| Relative humidity of drying gas (%) | 7 | 7 | 7 | 7 | 7 |
| Carbon dioxide concentration in drying gas (vol %) | 10 | 10 | 10 | 10 | 10 |
| Relative humidity of humid air at the outlet of paddle mixing apparatus (%) | 5 | 13 | 19 | 33 | 0.3 |
| Average particle size (μm) | 97 | 97 | 97 | 97 | 97 |
| Content of anhydrous sodium carbonate (mass %) | 0.38 | 0.31 | 0.26 | 0.15 | 0.42 |
| Content of sodium carbonate monohydrate (mass %) | 0.00 | 0.00 | 0.00 | 0.00 | 0.00 |
| Content of Wegscheider's salt (mass %) | 0.04 | 0.11 | 0.16 | 0.27 | 0.00 |
| Content of sodium sesquicarbonate (mass %) | 0.00 | 0.00 | 0.00 | 0.00 | 0.00 |
| Amount of particles weakly caked (mass %) | 8 | 3 | 9 | 33 | 96 |
| Amount of particles moderately caked (mass %) | 0 | 0 | 0 | 0 | 90 |
| Amount of particles strongly caked (mass %) | 0 | 0 | 0 | 0 | 69 |

Example 2

The packaging bag made of an LLDPE film of 120 μm used in Example 1 had a water vapor transmission rate of 6.0 g/(m²·24 h) at 40° C. with a relative humidity difference of 90% as stipulated in JIS K 7129. Instead, a dampproof packaging bag having alumina vapor-deposited thereon was used and the caking property evaluation test was carried out. As the structure of the packaging bag, a PET film having a thickness of 12 μm, and having an alumina transparent vapor deposition applied by the PVD method was used for dampproof for the outermost layer so that the vapor deposition layer faced inside, a nylon film having a thickness of 15 μm was used for the interlayer, and for the innermost layer, a completely additive-free LLDP film having a thickness of 70 μm was laminated by dry lamination. The vapor transmission of the packaging bag was 0.2 g/(m²·24 h) at 40° C. with a relative humidity difference of 90° C. as stipulated in JIS K 7129. As the sample for caking property evaluation test, No. 1 in Example 1 was used. The results are shown in Table 5. The results with respect to the dampproof bag correspond to No. 6. Caking could be prevented at a higher level. Further, no coloring of the product was observed on each of the samples in Examples 1 and 2. Further, each sample could pass through a metal detector.

TABLE 5

|  | No. | |
| --- | --- | --- |
|  | 1 | 6 |
| Average particle size (μm) | 97 | 97 |
| Content of anhydrous sodium carbonate (mass %) | 0.38 | 0.38 |
| Content of sodium carbonate monohydrate (mass %) | 0.00 | 0.00 |
| Content of Wegscheider's salt (mass %) | 0.04 | 0.04 |
| Content of sodium sesquicarbonate (mass %) | 0.00 | 0.00 |
| Amount of particles weakly caked (mass %) | 8 | 0 |
| Amount of particles moderately caked (mass %) | 0 | 0 |
| Amount of particles strongly caked (mass %) | 0 | 0 |

INDUSTRIAL APPLICABILITY

According to the present invention, various drawbacks resulting from caking of sodium hydrogencarbonate crystal particles used can be industrially avoided. Further, formation of sodium hydrogencarbonate crystal particles having a low caking property can be achieved by an easy means in a short time.

The entire disclosure of Japanese Patent Application No. 2004-195996 filed on Jul. 1, 2004 including specification, claims and summary is incorporated herein by reference in its entirety.

What is claimed is:

1. Sodium hydrogencarbonate crystal particles having a low caking property, which comprise sodium hydrogencarbonate crystal particles having an average particle size of from 50 to 500 μm based on the mass, and anhydrous sodium carbonate, and sodium carbonate monohydrate and/or Wegscheider's salt, present on the surface of the sodium hydrogencarbonate crystal particles in such amounts that the total content of anhydrous sodium carbonate, sodium carbonate monohydrate, Wegscheider's salt and sodium sesquicarbonate in the sodium hydrogencarbonate crystal particles is from 0.04 to 1 mass % as calculated as anhydrous sodium carbonate, anhydrous sodium carbonate accounts for at least 40 mass % of the total content, and sodium carbonate monohydrate and/or Wegscheider's salt accounts for from 5 to 60 mass % of the total content.

2. The sodium hydrogencarbonate crystal particles having a low caking property according to claim 1, wherein the total content of anhydrous sodium carbonate, sodium carbonate monohydrate, Wegscheider's salt and sodium sesquicarbonate in the sodium hydrogencarbonate crystal particles is from 0.1 to 0.9 mass % as calculated as anhydrous sodium carbonate, anhydrous sodium carbonate accounts for at least 40 mass % of the total content, and sodium carbonate monohydrate and/or Wegscheider's salt accounts for from 5 to 60 mass % of the total content.

3. A process for producing the sodium hydrogencarbonate crystal particles having a low caking property as defined in claim 1, which comprises subjecting sodium hydrogencarbonate crystal particles to heat treatment to convert part of the sodium hydrogencarbonate crystal particles into anhydrous sodium carbonate, followed by humidification to convert part of anhydrous sodium carbonate into sodium carbonate monohydrate and/or Wegscheider's salt.

4. The production process according to claim 3, wherein a slurry containing sodium hydrogencarbonate is obtained by crystallization, wet sodium hydrogencarbonate crystal particles are separated from the slurry, and the wet sodium hydrogencarbonate crystal particles are subjected to heat treatment.

5. A method of packaging sodium hydrogencarbonate crystal particles, which comprises packaging the sodium hydrogencarbonate crystal particles as defined in claim 1, in a material having a water vapor transmission rate of at most 5 g/(m²·24 h) at 40° C. with a relative humidity difference of 90% as stipulated in JIS K 7129.

6. The packaging method according to claim 5, wherein the material for packaging is a laminated sheet using a resin sheet obtained by vapor deposition treatment with alumina or silica.

7. The packaging method according to claim 6, wherein the innermost layer of the laminated sheet as the material for packaging, to be in contact with the sodium hydrogencarbonate crystal particles, is made of an additive-free polyethylene.

* * * * *

UNITED STATES PATENT AND TRADEMARK OFFICE
CERTIFICATE OF CORRECTION

PATENT NO. : 7,485,369 B2
APPLICATION NO. : 11/619411
DATED : February 3, 2009
INVENTOR(S) : Hirano et al.

It is certified that error appears in the above-identified patent and that said Letters Patent is hereby corrected as shown below:

On the title page, Item (75) should read:

-- (75) Inventors: Hachirou Hirano, deceased, late of Ichihara (JP); by Takako Hirano, legal representative, Chiba (JP); Shintaro Kikuchi, Kashima-gun (JP); Fumiaki Nakashima, Kashima-gun (JP); Hisakazu Arima, Kashima-gun (JP); Shigeru Sakurai, Chiyoda-ku (JP) --

Signed and Sealed this

Twenty-fourth Day of March, 2009

JOHN DOLL
*Acting Director of the United States Patent and Trademark Office*